US012558011B2

(12) United States Patent
Tsai et al.

(10) Patent No.: US 12,558,011 B2
(45) Date of Patent: Feb. 24, 2026

(54) DEVICE AND A METHOD FOR VOIDING DYSFUNCTION DIAGNOSIS

(71) Applicant: Feng Chia University, Taichung (TW)

(72) Inventors: Fang-Sheng Tsai, Taichung (TW);
Guan-Yu Peng, Taichung (TW);
Yu-Ting Tsai, Taichung (TW)

(73) Assignee: Feng Chia University, Taichung (TW)

( * ) Notice: Subject to any disclaimer, the term of this patent is extended or adjusted under 35 U.S.C. 154(b) by 0 days.

(21) Appl. No.: 19/211,423

(22) Filed: May 19, 2025

(65) Prior Publication Data

US 2025/0359793 A1     Nov. 27, 2025

(30) Foreign Application Priority Data

May 24, 2024    (TW) .................................. 113119414

(51) Int. Cl.
*A61B 5/20*         (2006.01)
*A61B 5/00*         (2006.01)
*G01N 29/02*        (2006.01)
*G01N 33/493*       (2006.01)

(52) U.S. Cl.
CPC ............ *A61B 5/202* (2013.01); *A61B 5/7267* (2013.01); *G01N 29/02* (2013.01); *G01N 33/493* (2013.01)

(58) Field of Classification Search
CPC .......... A61B 5/202; A61B 5/207; A61B 5/208
USPC ...................................................... 600/1, 587
See application file for complete search history.

(56) References Cited

U.S. PATENT DOCUMENTS

| | | | | |
|---|---|---|---|---|
| 9,810,686 B1 * | 11/2017 | Hall | ........................ | A61B 5/207 |
| 12,357,211 B2 * | 7/2025 | Loy | ...................... | A61B 5/6891 |
| 2009/0216099 A1 * | 8/2009 | Kim | ...................... | A61B 5/6887 |
| | | | | 600/509 |
| 2023/0105892 A1 * | 4/2023 | Barbedette | ........... | A61B 10/007 |
| | | | | 600/362 |

FOREIGN PATENT DOCUMENTS

| | | |
|---|---|---|
| CN | 107660136 A | 2/2018 |
| CN | 112739262 A | 4/2021 |
| EP | 2023819 B1 | 10/2009 |
| JP | 2023104013 A | 7/2023 |
| TW | 202384 B | 3/1993 |

* cited by examiner

*Primary Examiner* — Rene T Towa
*Assistant Examiner* — Noah M Healy
(74) *Attorney, Agent, or Firm* — Best & Flanagan LLP

(57) ABSTRACT

The present invention is related to a device and a system for voiding dysfunction diagnosis. By detecting a vibration signal generated by the urine from a patient who suffers from urinary dysfunction, the present invention could efficiently and accurately detect and monitor the condition of the patient. The present invention can be introduced to actual clinical applications achieving continuous monitoring urination status for the patient for home care. The present invention could also provide urinary medication efficiency or urinary status of the patient before or after prostate surgery.

11 Claims, 4 Drawing Sheets

DEVICE AND A METHOD FOR VOIDING DYSFUNCTION DIAGNOSIS

FIELD OF INVENTION

The present invention relates to a device and a system for voiding dysfunction diagnosis, and more particularly to a device and system that enables the diagnosis of voiding dysfunction in a non-invasive approach and practical manner.

BACKGROUND OF THE INVENTION

Lower urinary tract symptoms (LUTS) are common urological problems that affect hundreds of millions of people worldwide. In clinical practice, the diagnosis and treatment of patients suffering from voiding dysfunction primarily rely on monitoring the urination behavior of patients, which includes maintaining a voiding diary at home or undergoing uro-dynamic testing via a hospital visiting. However, the former approach depends on self-reporting by the patient, which lacks objectivity and is highly susceptible to data loss. The latter method is invasive and requires expensive equipment, which limits the frequency of measurements and reduces patient compliance.

In view of the above, there is an urgent need for a monitoring device that can effectively address the diagnostic challenges associated with voiding dysfunction caused by LUTS, thereby improving the quality of medical care. Hence, it is eager to have a solution that will overcome or substantially ameliorate at least one or more of the deficiencies of a prior art, or to at least provide an alternative solution to the problems. It is to be understood that, if any prior art information is referred to herein, such reference does not constitute an admission that the information forms part of the common general knowledge in the art.

SUMMARY OF THE INVENTION

In order to solve shortcomings of the inaccuracy of self-monitoring in patients with voiding dysfunction and the high cost of uro-dynamic testing in hospitals, the present invention provides a voiding dysfunction diagnosis device.

From top to bottom, the device comprises a splash guard, a top plate, an annular seat, and a bottom plate. A housing space is defined between the top plate, the annular seat, and the bottom plate, wherein: the annular seat is ring-shaped and comprises an upper portion and a lower portion. Several protruding ribs are arranged on the inner sidewall, each protruding rib containing a screw hole. A top portion of the annular seat extends inward to form an eave structure.

The top plate is arranged within an inner diameter of the top portion of the annular seat and abuts an underside of the eave structure. The periphery of the top plate is provided with a plurality of insertion grooves corresponding to the positions of the ribs on the annular seat.

The top plate comprises an upper surface and a lower surface. A vibration sensor and a controller module are fixedly installed on the lower surface of the top plate. A plurality of elastic elements are arranged between the top plate and the bottom plate. The lower surface of the top plate is provided with a plurality of mounting portions protruding toward the bottom plate. Each elastic element is embedded in and fixed to the mounting portion, securing the top and bottom plates. The elastic elements press the top plate against the underside of the eave structure.

The splash guard is a solid arc-shaped dome having a domed upper surface and a shock-absorbing bottom. The splash guard is affixed to the upper surface of the top plate via the shock-absorbing bottom.

The bottom plate corresponds in size and shape to the outer diameter of the annular seat and is provided with multiple screw holes at positions corresponding to the ribs of the annular seat. The bottom plate is secured to the annular seat using screws.

In accordance, the present invention has the following advantages:

The present invention provides an innovative auxiliary detection and diagnostic device and system. By sensing a non-contact vibration signal generated by urine discharged from a patient suffering from voiding dysfunction into the device of the present invention, the system can achieve high-accuracy monitoring performance. The present invention can be applied in actual clinical used, enabling continuous at-home monitoring of voiding conditions and providing clinicians with essential information regarding the effects of urinary medication or the urination status before and after prostate surgery. The monitoring system proposed by the present invention is low-cost, compact, and capable of providing real-time results, making it suitable for home care. Furthermore, the present invention provides a real-time, remote, and continuous symptom monitoring device. The systematically collected data can assist in diagnosing voiding dysfunction-related diseases and facilitate integration with large-scale databases and various data sources.

When the splash guard and the top plate of the voiding dysfunction diagnosis device of the present invention are bonded together using an adhesive, and damage occurs during use, the splash guard and top plate can be replaced simply by disassembling the bottom plate and removing the sensor and circuitry, thereby extending the product's service life. Additionally, each component of the present invention can be made of environmentally friendly biodegradable materials and designed as disposable units, ensuring hygiene and environmental cleanliness.

Many of the attendant features and advantages of the present invention will become better understood with reference to the following detailed description considered in connection with the accompanying figures and drawings.

BRIEF DESCRIPTION OF THE DRAWINGS

The steps and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

Figure 1:
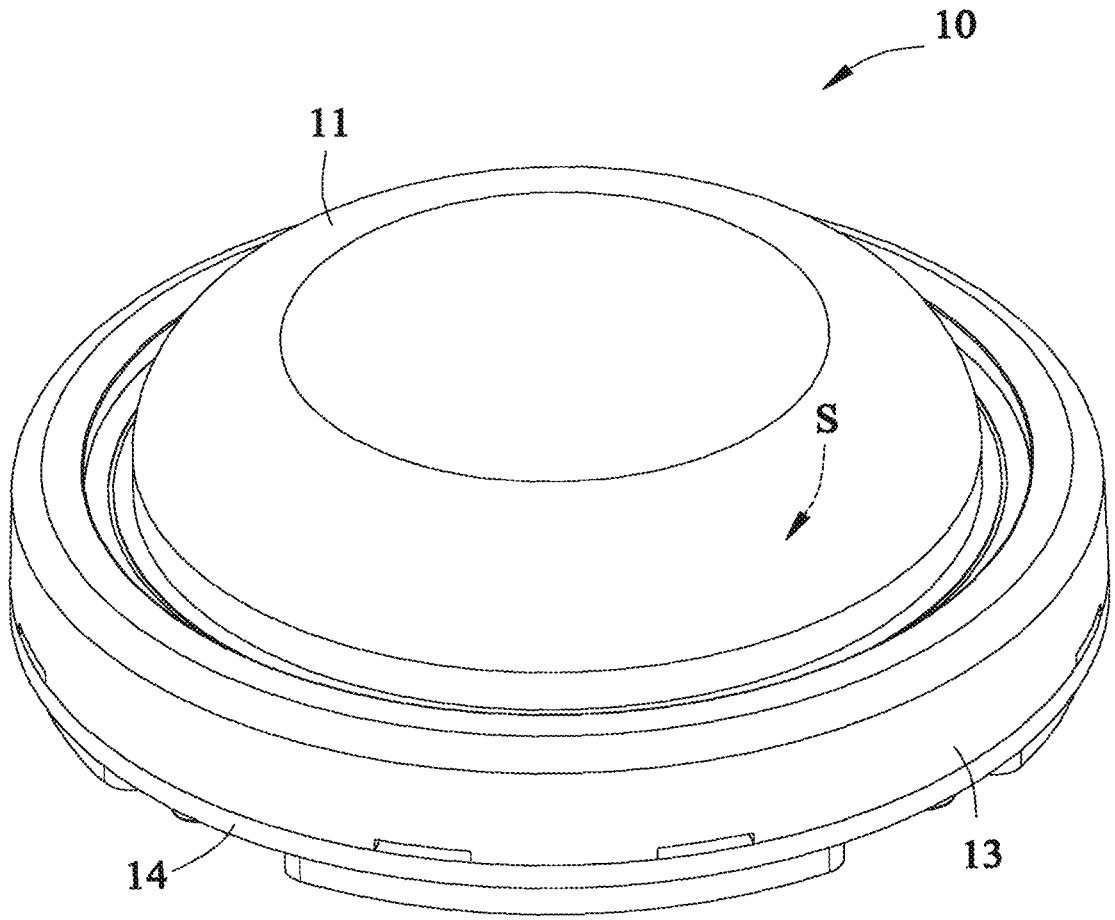
FIG. 1 is a schematic view of a preferred embodiment of the voiding dysfunction diagnosis device in accordance to the present invention.

Reference will now be made in detail to the present preferred embodiments of the invention, examples of which are illustrated in the accompanying drawings. Wherever possible, the same reference numbers are used in the drawings and the description to refer to the same or like parts. It is not intended to limit the method by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details. As used in the description herein and throughout the claims that follow, the meaning of "a", "an", and "the" may include reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to.

<Voiding Dysfunction Diagnosis Device>

Figure 2:
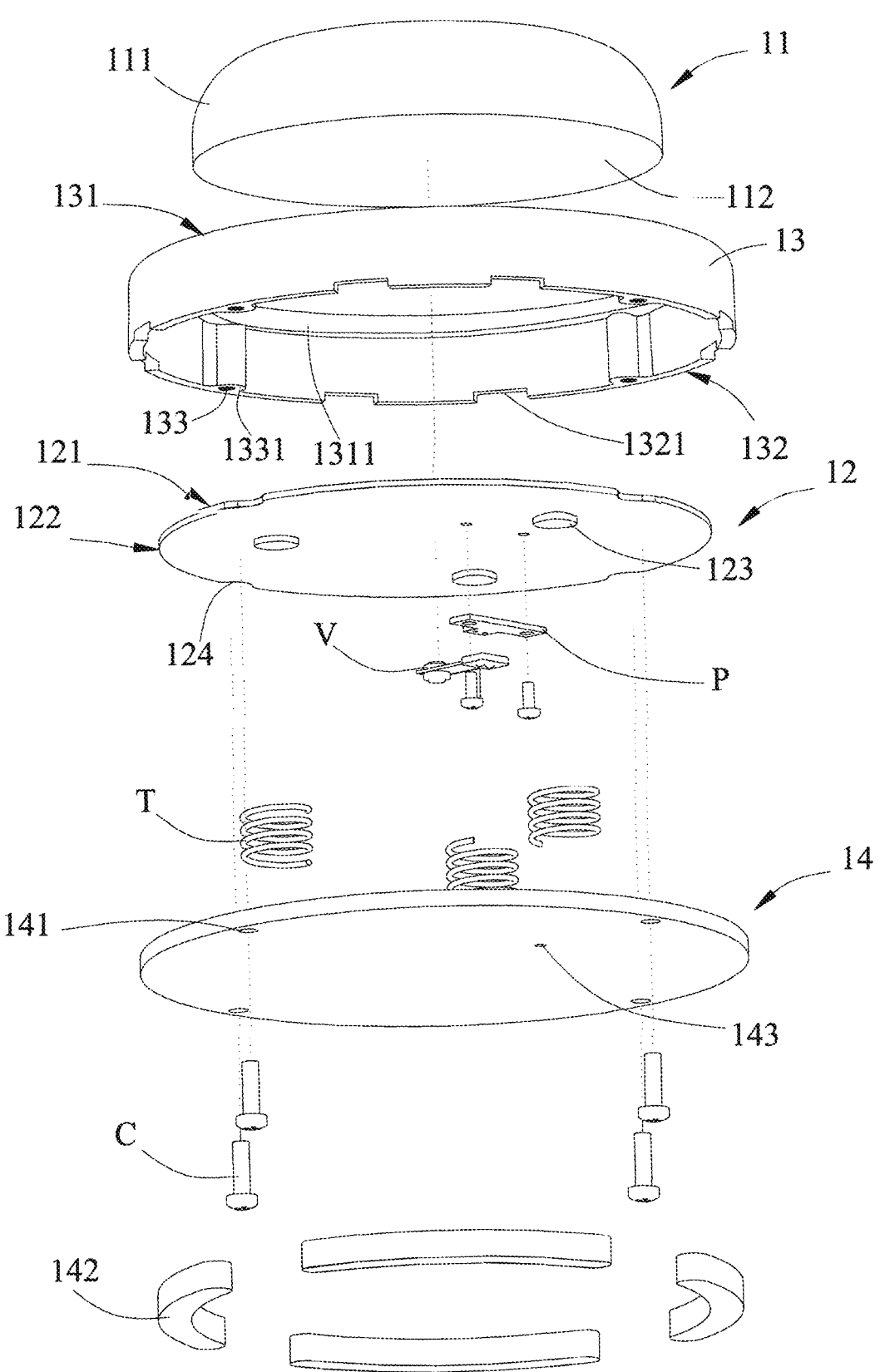
FIG. 2 is an exploded view of a preferred embodiment of the voiding dysfunction diagnosis device in accordance to the present invention.

Please refer to FIGS. 1 and 2, which illustrate a preferred embodiment of the voiding dysfunction diagnosis device 10 of the present invention. From top to bottom, the device includes a splash guard 11, a top plate 12, an annular seat 13, and a bottom plate 14. A housing space S is formed between the top plate 12, the annular seat 13, and the bottom plate 14.

The annular seat 13 is ring-shaped and comprises an upper portion and a lower portion 132. Several protruding ribs 133 are provided on an inner sidewall of the annular seat 13, each of which includes a screw hole 1331. In a preferred embodiment, an eave structure 1311 is extended inwardly formed from the upper portion 131 toward a center of the ring. In another preferred embodiments, the eave structure 1311 may be formed discontinuously around the ring of the annular seat 13. The lower portion 132 of the annular seat 13 is provided with at least one slit 1321.

The top plate 12 has a dimension and shape corresponded to or slightly smaller than an inner diameter of the annular seat 13 and is positioned within the inner diameter of the upper portion 131, touching the underside of the eave structure 1311. A periphery of the top plate 12 is provided with a plurality of insertion grooves 124, each positioned corresponding with a rib 133 of the annular seat 13, thereby enabling proper placement within the inner diameter of the upper portion 131.

The top plate 12 comprises an upper surface 121 and a lower surface 122. A vibration sensor V and a controller module P are mounted on the lower surface 122, either by adhesive or mechanical fasteners. The controller module P preferably receives vibration signals from the vibration sensor V, analyzes and transmits the results via any conventional wired or wireless connection to a cloud database. Preferably, the vibration signal from the vibration sensor V is amplified by a signal amplifier before being sent to the controller module P.

In a preferred embodiment, the vibration sensor V comprises a cantilever-type sensor such as the Minisense 100. The controller module P is preferably an ESP32 module, which can transmit data via Wi-Fi, Bluetooth, or wired connection.

Preferably, a plurality of elastic elements T are disposed between the top plate 12 and the bottom plate 14. To secure these elastic elements T, the lower surface 122 of the top plate 12 is provided with a plurality of mounting portions 123 protruding toward the bottom plate 14. The elastic elements T, preferably springs, are embedded in the mounting portions 123 and fixed between the top plate 12 and the bottom plate 14. An elastic restoring force generated upon compression of the elastic elements T allows the top plate 12 remain touching or attaching to the underside of the eave structure 1311.

The splash guard 11 is a solid arc-shaped dome having a domed upper surface 111 and a shock-absorbing bottom 112. The shape of the shock-absorbing bottom 112 corresponds to or is slightly smaller than that of the top plate 12, and it is fixed to the upper surface 121 of the top plate 12 using an adhesive or any fasteners.

The bottom plate 14 has a dimension and shape corresponded to an outer diameter of the annular seat 13 and is provided with multiple screw holes 141 positioned to align with the protruding ribs 133 of the annular seat 13. The bottom plate 14 is secured to the annular seat 13 using multiple screws C. Preferably, the bottom of the bottom plate 14 is equipped with a plurality of shock-absorbing elements 142. The bottom plate 14 may also include an opening 143 to allow external cable connection to any external system.

Figure 3A:
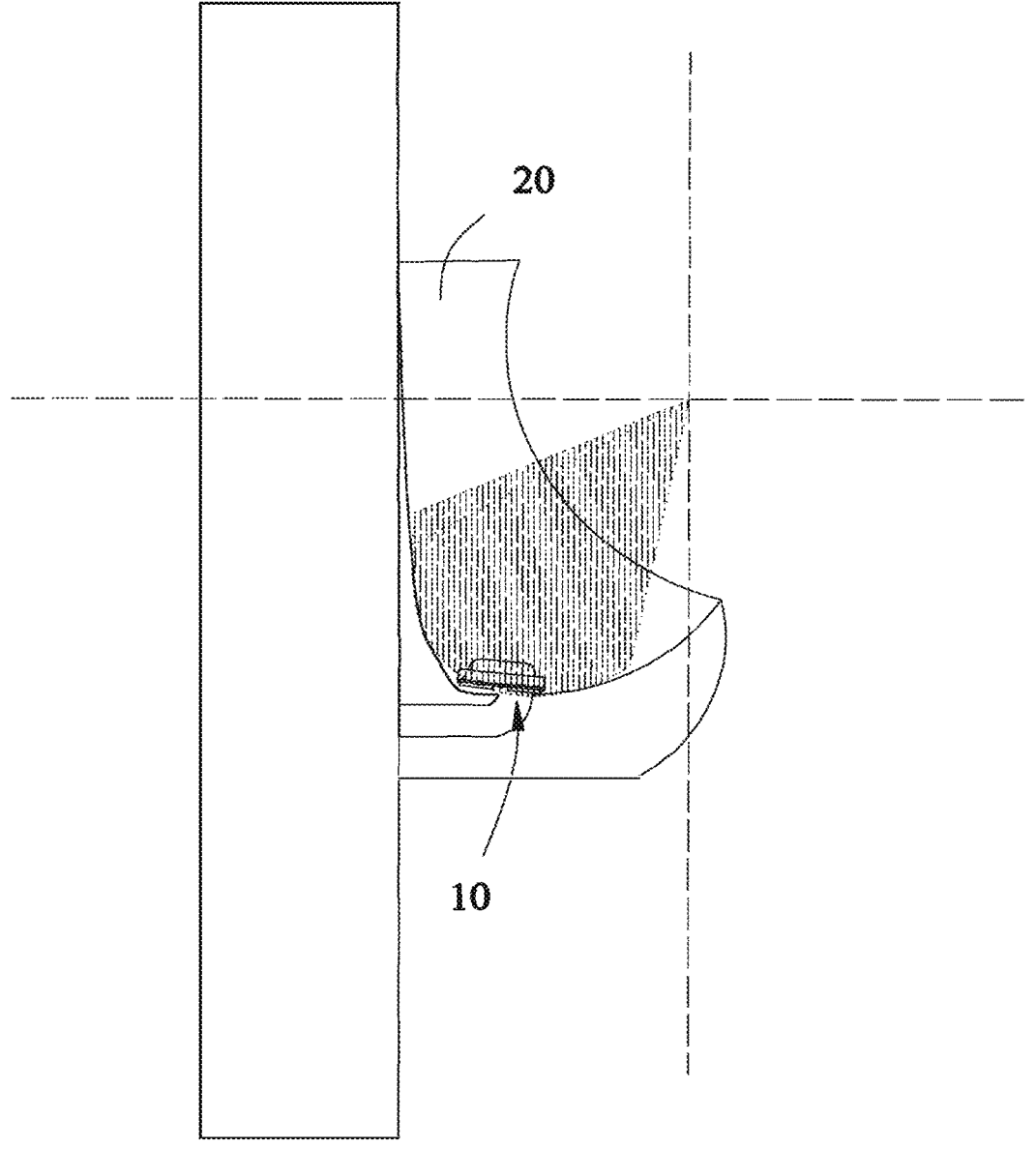
FIGS. 3a and 3b are usage schematic diagrams of the preferred embodiment of the voiding dysfunction diagnosis device in accordance to the present invention.
Figure 3B:
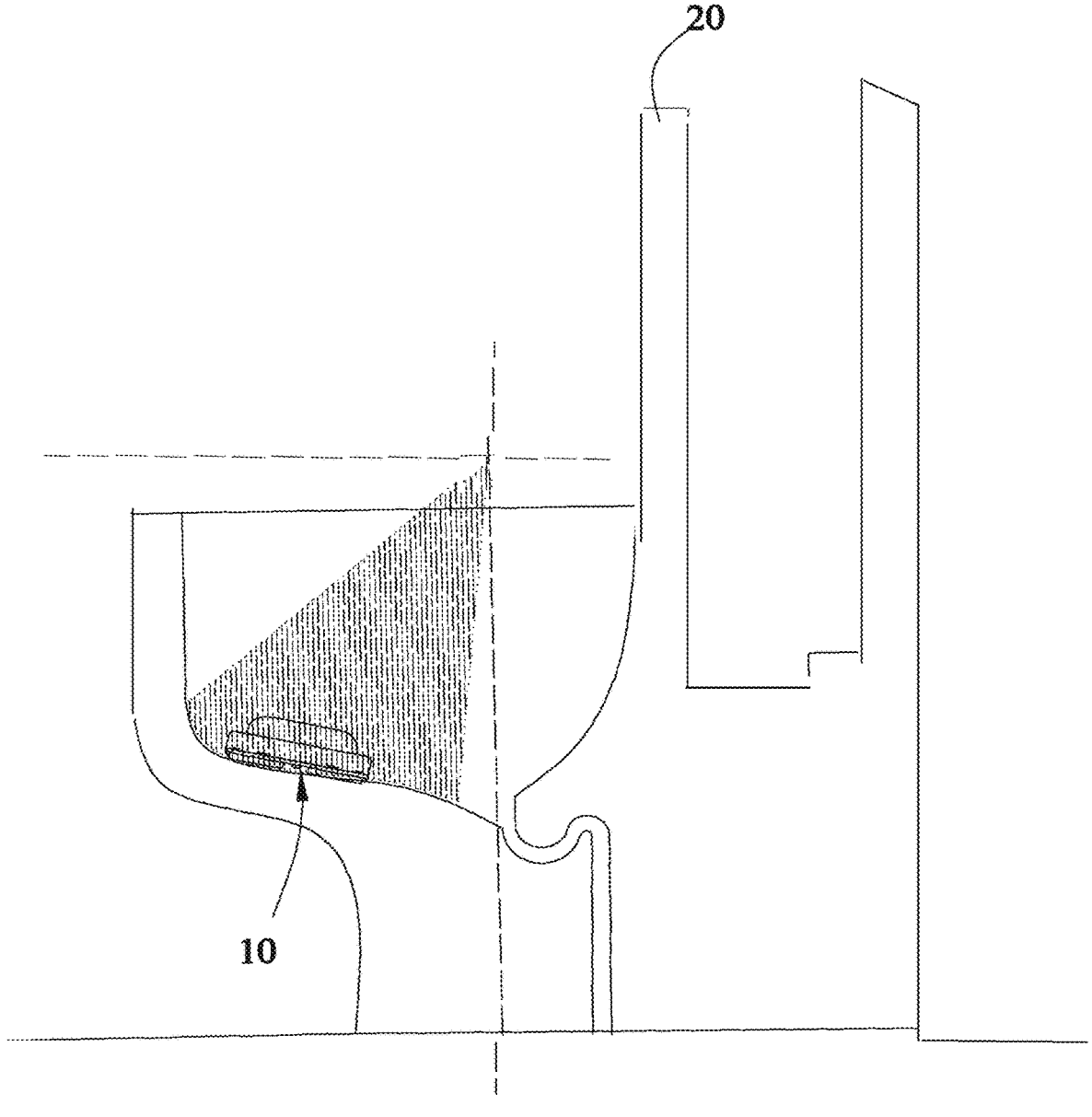

Please refer to FIGS. 3a and 3b, which illustrate the voiding dysfunction diagnosis device 10 of the present invention installed in a toilet 20. The toilet 20 may be a male urinal for standing urination (as shown in FIG. 3a) or a seated toilet (as shown in FIG. 3b). The device 10 is preferably installed within the user's urine trajectory. In the case of the urinal in FIG. 3a, it is preferably installed at the bottom collection area; in the case of the seated toilet in FIG. 3b, it is preferably installed slightly forward to better receive the user's urine. The splash guard 11 is designed to prevent urine splashing during use, which may otherwise interfere with sensor accuracy.

The slit 1321 at the bottom of the annular seat 13 allows for a discharge of any urine accumulated within the housing space S of the present invention.

The present invention further provides a voiding dysfunction diagnosis system that utilizes the above-described voiding dysfunction diagnosis device 10. The system comprises:

installing the voiding dysfunction diagnosis device 10 on a urinal apparatus;

receiving a user's urine through the voiding dysfunction diagnosis device 10;

the vibration sensor V detects the vibration caused by urination and transmits vibration data to the controller module P for analysis; and displaying the analysis results on a display interface.

The controller module P analyzes the vibration data in conjunction with an artificial intelligence machine learning module to diagnose different urination patterns, such as urine volume analysis, peak flow rate analysis, urination duration analysis, or instantaneous flow analysis.

Preferably, the analysis results of the controller module P are uploaded to a cloud server and subsequently transmitted to a remote display interface, such as an application on a mobile phone, tablet, or computer.

The above specification, examples, and data provide a complete description of the present disclosure and use of exemplary embodiments. Although various embodiments of the present disclosure have been described above with a certain degree of particularity, or with reference to one or more individual embodiments, those with ordinary skill in the art could make numerous alterations or modifications to the disclosed embodiments without departing from the spirit or scope of this disclosure.

What is claimed is:

1. A voiding dysfunction diagnosis device, comprising, in order from top to bottom, a splash guard, a top plate, an annular seat, and a bottom plate; a housing space is formed between the top plate, the annular seat, and the bottom plate, wherein:

the annular seat is ring-shaped and comprises an upper portion and a lower portion, the inner sidewall of which includes a plurality of ribs, each rib having a screw hole; the upper portion of the annular seat extends inward to form an eave structure;

the top plate is disposed within an inner diameter of the upper portion of the annular seat and abuts an underside of the eave structure; the periphery of the top plate is provided with a plurality of insertion grooves, the positions of which correspond to the ribs on the annular seat;

the top plate includes a top surface and a bottom surface; a vibration sensor and a controller module are fixedly disposed on the bottom surface of the top plate; a plurality of elastic elements are provided between the top plate and the bottom plate; the bottom surface of the top plate includes a plurality of protruding mounting portions directed toward the bottom plate; the elastic elements are embedded in and fixed between the top plate and the bottom plate; the elastic elements bias the top plate against the eave structure;

the splash guard is a solid arc-shaped dome having a domed top surface and a shock-absorbing bottom, the bottom surface being affixed to the top surface of the top plate; and the bottom plate is sized and shaped to correspond to the outer diameter of the annular seat and includes a plurality of screw holes aligned with the ribs of the annular seat and is fixed to the annular seat using a plurality of screws.

2. The voiding dysfunction diagnosis device of claim 1, wherein the elastic elements comprise springs.

3. The voiding dysfunction diagnosis device of claim 1, wherein the splash guard is affixed to the top surface of the top plate using adhesive.

4. The voiding dysfunction diagnosis device of claim 1, wherein the bottom of the bottom plate includes a plurality of shock-absorbing elements.

5. The voiding dysfunction diagnosis device of claim 1, wherein the bottom plate includes a opening.

6. A voiding dysfunction diagnosis method, comprising:
installing the voiding dysfunction diagnosis device of claim 1 on a urination fixture;
receiving urine through the voiding dysfunction diagnosis device;
detecting urination vibrations with the vibration sensor and transmitting vibration data to the controller module for analysis; and
displaying the analysis results on a display interface.

7. The voiding dysfunction diagnosis method of claim 6, wherein the analysis results of the controller module are uploaded to a cloud server and then transmitted to a remote display interface.

8. The voiding dysfunction diagnosis method of claim 6, wherein the controller module receives the vibration signal transmitted by the vibration sensor, analyzes the results, and transmits the results to a cloud database via wired or wireless communication.

9. The voiding dysfunction diagnosis method of claim 6, wherein the vibration signal from the vibration sensor is amplified by a signal amplifier before being transmitted to the controller module.

10. The voiding dysfunction diagnosis method of claim 6, wherein the vibration sensor comprises a cantilever-type vibration sensor.

11. The voiding dysfunction diagnosis method of claim 6, wherein the controller module is an ESP32 module.

* * * * *